United States Patent [19]

Nagano et al.

[11] Patent Number: 4,826,533
[45] Date of Patent: May 2, 1989

[54] N-(SUBSTITUTED PHENYL)-TETRAHYDROPHTHALIMIDE COMPOUNDS, AND THEIR PRODUCTION AND HERBICIDE USE

[75] Inventors: Eiki Nagano, Nishinomiya; Shunichi Hashimoto, Toyonaka; Ryo Yoshida, Kawanishi; Hiroshi Matsumoto, Toyonaka; Katsuzo Kamoshita, Toyono, all of Japan

[73] Assignee: Sumitomo Chemical Company, Limited, Osaka, Japan

[21] Appl. No.: 102,615

[22] Filed: Sep. 30, 1987

Related U.S. Application Data

[63] Continuation of Ser. No. 887,970, Jul. 21, 1986, Pat. No. 4,770,695, Continuation of Ser. No. 445,726, Nov. 30, 1982, abandoned.

[30] Foreign Application Priority Data

| Dec. 25, 1981 | [JP] | Japan | 56-212396 |
| Feb. 5, 1982 | [JP] | Japan | 57-17858 |
| Feb. 19, 1982 | [JP] | Japan | 57-13845 |
| Mar. 23, 1982 | [JP] | Japan | 57-46940 |
| May 6, 1982 | [JP] | Japan | 57-76306 |

[51] Int. Cl.⁴ .................. A01N 43/38; C07D 209/48
[52] U.S. Cl. .......................... 71/96; 548/513
[58] Field of Search ............... 548/513; 71/96

[56] References Cited

U.S. PATENT DOCUMENTS

| 3,235,605 | 2/1966 | Napolitano | 71/96 |
| 3,465,001 | 9/1969 | Bolhofer et al. | 548/549 |
| 3,808,230 | 4/1974 | Podesva et al. | 71/96 |
| 3,878,224 | 4/1975 | Matsui et al. | 71/96 |
| 3,954,442 | 5/1976 | Becker et al. | 71/108 |
| 3,984,435 | 10/1976 | Matsui et al. | 548/513 |
| 4,001,272 | 4/1977 | Goddard | 71/96 |
| 4,032,326 | 6/1977 | Goddard | 71/96 |
| 4,124,375 | 11/1978 | Bollinger et al. | 71/96 |
| 4,292,070 | 9/1981 | Wakabayashi et al. | 71/96 |
| 4,349,377 | 9/1982 | Durr et al. | 71/98 |
| 4,431,822 | 2/1984 | Nagano | 548/513 |
| 4,439,229 | 3/1984 | Swithenbank | 548/549 |
| 4,595,409 | 6/1986 | Haga et al. | 71/96 |
| 4,670,046 | 6/1987 | Nagano | 71/96 |
| 4,684,397 | 8/1987 | Nagano et al. | 71/96 |
| 4,709,049 | 11/1987 | Nagano et al. | 71/96 |

FOREIGN PATENT DOCUMENTS

| 0049508 | 4/1982 | European Pat. Off. . |
| 0049511 | 4/1982 | European Pat. Off. . |
| 0067352 | 12/1982 | European Pat. Off. . |
| 077938 | 5/1983 | European Pat. Off. . |
| 083055A | 7/1983 | European Pat. Off. . |
| 0095192 | 12/1983 | European Pat. Off. . |
| 0126419 | 6/1985 | European Pat. Off. . |
| 2433013A | 7/1984 | France . |
| 55-130954 | 11/1980 | Japan . |
| 57-24355 | 4/1982 | Japan . |
| 213814 | 9/1978 | U.S.S.R. . |
| 2005668 | 4/1979 | United Kingdom . |
| 2046754 | 8/1980 | United Kingdom . |

OTHER PUBLICATIONS

Pagane, J. Am. Chem. Soc., vol. 81, pp. 94–101 (1959).
G. Pagano et al, Chem. Abst. 89:42719j (1978).
C. Swithenbank, Chem. Abst. 98:215478w (1983).
R. Giraudon, Chem. Abst. 93:114150z (1980).
R. Morrison et al., Org. Chemistry, 2nd Ed., p. 602.
G. Pagano et al, Il Farmaco—Ed. Sc., vol. 33, pp. 332–349.
Chemical Abstract 101, 146132v.
Chemical Abstract 101, 124918d.
Chemical Abstract 101, 124919e.
PCT Publication WO80/00341.

*Primary Examiner*—Mark L. Berch
*Attorney, Agent, or Firm*—Birch, Stewart, Kolasch & Birch

[57] ABSTRACT

A tetrahydrophthalimide compound of the formula:

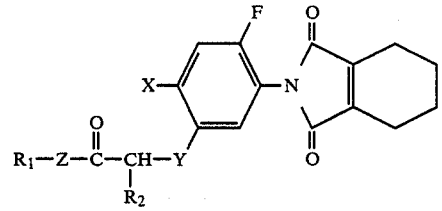

wherein $R_1$ is hydrogen, alkyl, lower cycloalkyl, lower alkyl(lower)cycloalkyl, lower cycloalkyl(lower)alkyl, lower alkoxy(lower)alkyl, lower alkenyl, lower cycloalkenyl, lower cycloalkenyl(lower)alkyl, phenyl, cyano(lower)alkyl, lower alkynyl, lower alkylideneamino, lower alkylthio(lower)alkyl, benzyl, halo(lower)alkyl or lower cycloalkylideneamino, $R_2$ is hydrogen, lower alkyl or lower alkoxy, X is chlorine or bromine, Y is oxygen or imino and Z is oxygen or sulfur. The tetrahydrophthalimide compound is useful as a herbicide.

21 Claims, No Drawings

N-(SUBSTITUTED PHENYL)-TETRAHYDROPHTHALIMIDE COMPOUNDS, AND THEIR PRODUCTION AND HERBICIDE USE

This application is a divisional of application Ser. No. 887,970, filed on July 21, 1986, now U.S. Pat. No. 4,770,695, which is a continuation of application Ser. No. 445,726, filed on Nov. 30, 1982, now abandoned.

The present invention relates to tetrahydrophthalimide compounds, and their production and use.

The tetrahydrophthalimide compounds (hereinafter referred to as "tetrahydrophthalimide(s)") are represented by the formula:

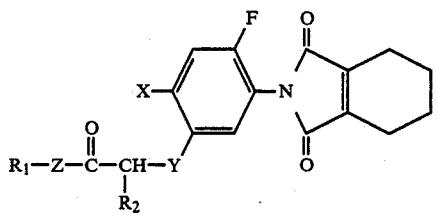

wherein $R_1$ is hydrogen, alkyl, lower cycloalkyl, lower alkyl(lower)cycloalkyl, lower cycloalkyl(lower)alkyl, lower alkoxy(lower)alkyl, lower alkenyl, lower cycloalkenyl, lower cycloalkenyl(lower)alkyl, phenyl, cyano(lower)alkyl, lower alkynyl, lower alkylideneamino, lower alkylthio(lower)alkyl, benzyl, halo(lower)alkyl or lower cycloalkylideneamino, $R_2$ is hydrogen, lower alkyl or lower alkoxy, X is chlorine or bromine, Y is oxygen or imino and Z is oxygen or sulfur.

In the above, the number of carbon atoms in the alkyl group is not more than 12. The term "lower" is generally intended to have not more than 8 carbon atoms, preferably 3 to 7 carbon atoms for a cyclic moiety and not more than 6 carbon atoms for a non-cyclic moiety. Preferred numbers of carbon atoms for lower alkyl, lower cycloalkyl, lower alkenyl, lower cycloalkenyl and lower alkynyl are respectively from 1 to 6, from 3 to 7, from 2 to 6, from 5 to 6 and from 2 to 6. Preferable numbers of carbon atoms for lower alkoxy, lower alkylthio, lower alkylideneamino and lower cycloalkylideneamino are respectively from 1 to 6, from 1 to 6, from 1 to 6 and from 3 t 7. More preferably, lower cycloalkyl, lower alkyl(lower)cycloalkyl, lower cycloalkyl(lower)alkyl, lower alkoxy(lower)alkyl, lower alkenyl, lower cycloalkenyl, lower cycloalkenyl(lower)alkyl, cyano(lower)alkyl, lower alkynyl, lower alkylideneamino, lower alkylthio(lower)alkyl, halo(lower)alkyl and lower cycloalkylideneamino represented by $R_1$ may be respectively $C_3$–$C_7$ cycloalkyl, $C_1$–$C_2$ alkyl($C_3$–$C_6$)cycloalkyl, $C_3$–$C_6$ cycloalkyl($C_1$–$C_2$)alkyl, $C_1$–$C_4$ alkoxy($C_1$–$C_4$)alkyl, $C_2$–$C_4$ alkenyl, $C_5$–$C_6$ cycloalkenyl, $C_5$–$C_6$ cycloalkenyl($C_1$–$C_2$)alkyl, cyano($C_1$–$C_3$)alkyl, $C_3$–$C_4$ alkynyl, $C_1$–$C_4$ alkylideneamino, $C_1$–$C_4$ alkylthio($C_1$–$C_4$)alkyl, halo($C_1$–$C_4$)alkyl and $C_4$–$C_6$ cycloalkylideneamino; and lower alkyl and lower alkoxy represented by $R_2$ may be respectively $C_1$–$C_3$ alkyl and $C_1$–$C_2$ alkoxy.

It is known that some tetrahydrophthalimide compounds exhibit a herbicidal activity. For instance, U.S. Pat. No. 3,984,435, EP No. 0049508A, U.S. Pat. No. 4,032,326, etc. disclose that 2-(4-chlorophenyl)-4,5,6,7-tetrahydro-2H-isoindole-1,3-dione, 2-[4-chloro-3-(1-propylthiocarbonylbutoxy)phenyl]-4,5,6,7-tetrahydro-2H-isoindole-1,3-dione, 2-(4-chloro-2-fluoro)-4,5,6,7-tetrahydro-2H-isoindole-1,3-dione, etc. are useful as herbicides. However, their herbicidal effect is not always satisfactory.

It has now been found that the tetrahydrophthalimides (I) show a strong herbicidal activity against a wide variety of weeds by foliar or soil treatment in plowed fields. Advantageously, some do not produce any material phytotoxicity on agricultural crops (e.g. corn, soybean, cotton). The herbicidal activity of the tetrahydrophthalimides (I) is particularly notable on post-emergence foliar treatment of broad-leaved weeds such as common purslane (*Portulaca oleracea*), common lambsquarters (*Chenopodium album*), redroot pigweed (*Amaranthus retroflexus*), hemp sesbania (*Sesbania exaltata*), velvetleaf (*Abtilon theophrasti*), prickly sida (*Sida spinosa*), ivyleaf morningglory (*Ipomoea hederacea*), tall morningglory (*Ipomoea purpurea*), field bindweed (*Convolvulus arvensis*), jimsonweed (*Datura stramonium*), black nightshade (*Solanum nigrum*), cocklebur (*Xanthium pensylvanicum*), sunflower (*Helianthus annus*), common ragweed (*Ambrosia artemisifolia*) in corn or soybean fields as they do not afford any toxicity to corn or soybean. Likewise, the tetrahydrophthalimides (I) exhibit a good herbicidal activity against Graminaceous weeds such as barnyardgrass (*Echinochloa crus-galli*), broad-leaved weeds such as false pimpernel (*Lindernia procumbens*), toothcup (*Rotala indica*) and waterwort (*Elatine triandra*) and paddy field weeds such as nutsedge (*Cyperus serotinus*), monochoria (*Monochoria vaginalis*) and arrowhead (*Sagittaria pygmaea*) in paddy rice fields, while exerting no significant damage to rice plants. Accordingly, the tetrahydrophthalimides (I) can be used as herbicides applicable to paddy fields as well as agricultural plowed fields. The tetrahydrophthalimides (I) are also useful as herbicides to be employed for orchards, pastures, lawns, forests, non-agricultural fields, etc.

Among the tetrahydrophthalimides (I) of the present invention, favorable are those of the formula (I) wherein $R_2$ is hydrogen or lower alkyl. More favorable are those of formula (I) wherein $R_2$ is hydrogen or methyl. Most favorable are those of the formula (I) wherein $R_2$ is hydrogen as they show a high selectivity to soybean or corn by foliar treatment.

The tetrahydrophthalimides (I) can be produced by reacting a HY-phenyltetrahydrophthalimide of the formula:

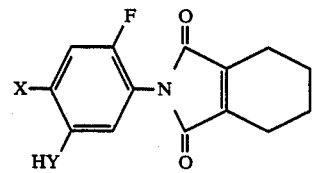

wherein X and Y are each as defined above with an α-halocarboxylic acid ester of the formula:

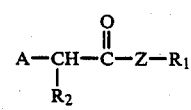

wherein A is chlorine or bromine and $R_1$, $R_2$ and Z are each as defined above in a solvent in the presence or absence of a dehydrohalogenating agent, usually at a temperature of 0° to 200° C. for 1 to 240 hours. The amounts of the α-halo-carboxylic acid ester (III) and the dehydrohalogenating agent may be respectively 1.0 to 10 equivalents and 0.5 to 1.5 equivalents to the HY-phenyltetrahydrophthalimide (II). When desired, a phase transfer catalyst such as tetrabutyl-ammonium bromide or benzyltributylammonium chloride may be employed.

As the solvent, there may be used an aliphatic hydrocarbon (e.g. hexane, heptane, ligroin, petroleum ether), an aromatic hydrocarbon (e.g. benzene, toluene, xylene), a halogenated hydrocarbon (e.g. chloroform, carbon tetrachloride, dichloroethane, chlorobenzene, dichlorobenzene), an ether (e.g. diethyl ether, diisopropyl ether, dioxane, tetrahydrofuran, diethylene glycol dimethyl ether), a ketone (e.g. acetone, methylethylketone, methylisobutylketone, isophorone, cyclohexanone), an alcohol (e.g. methanol, ethanol, isopropanol, t-butanol, octanol, cyclohexanol, methylcellosolve, diethylene glycol, glycerol), a nitrile (e.g. acetonitrile, isobutyronitrile), an acid amide (e.g. formamide, N,N-dimethylformamide, acetamide), a sulfur compound (e.g. dimethylsulfoxide, sulfolane), water, etc. These solvents may be employed alone or in combination.

Examples of the dehydrohalogenating agents are an organic base (e.g. pyridine, triethylamine, N,N-diethylaniline), an inorganic base (e.g. sodium hydroxide, potassium hydroxide, sodium carbonate, potassium carbonate, sodium hydride), an alkali metal alkoxide (e.g. sodium methoxide, sodium ethoxide), etc.

The produced tetrahydrophthalimides (I) can be purified by conventional procedures, such as chromatography, recrystallization or the like.

The starting HY-phenyltetrahydrophthalimide (II: Y=NH) can be produced by treating a nitrophenyltetrahydrophthalimide of the formula:

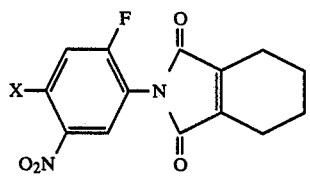

(IV)

wherein X is as defined above with 2.0 to 10 equivalents of an iron in the presence of an acid in a solvent (e.g. acetic acid, water, methanol, ethanol, tetrahydrofuran) at a temperature of 20° to 100° C.

The production of the nitrophenyltetrahydrophtalimide (IV) is summarized in the following scheme:

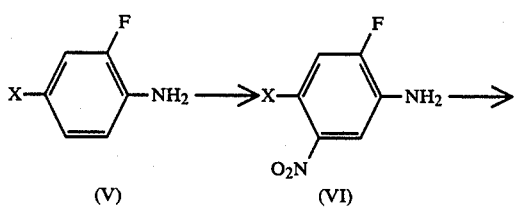

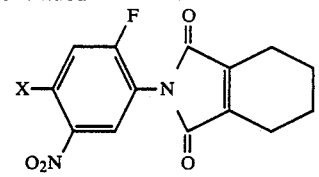

(IV)

wherein X is as defined above.

Namely, the haloaniline (V) is treated with 1.0 to 1.5 equivalents of conc. nitric acid in conc. sulfuric acid at a temperature of 10° to −10° C. to give the nitroaniline (VI), which is then reacted with 3,4,5,6-tetrahydrophthalic anhydride in a solvent (e.g. toluene, xylene, acetic acid, propionic acid, water, dioxane) at a temperature of 0° to 200° C., whereby the nitrophenyltetrahydrophthalimide (IV) is obtained.

The thus obtained compound (IV) may be subjected to usual work-up or, if necessary, to purification by chromatography, recrystallization or the like.

The starting HY-phenyltetrahydrophthalimide (II: Y=O) can be produced as well by reacting a phenol of the formula:

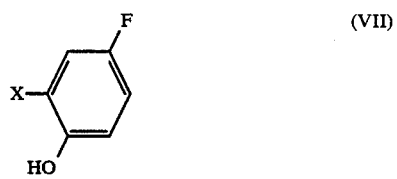

(VII)

wherein X is as defined above according to the following scheme:

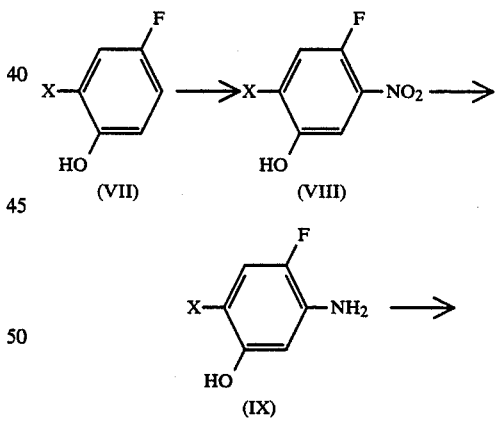

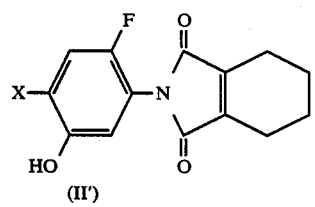

(II')

wherein X is as defined above.

Namely, the hydroxyphenyltetrahydrophthalimide (II') can be manufactured from the phenol (VII) by nitrating the same, reducing the resultant nitrophenol (VIII) and reacting the resulting aminophenol (IX) with 3,4,5,6-tetrahydrophthalic anhydride.

Conversion of the phenol (VII) into the nitrophenol (VIII) may be accomplished by application of a conventional nitration procedure to the former. Usually, however, the indirect nitration which consists of the following three steps is favorable in the achievement of the selective nitration at the desired position:

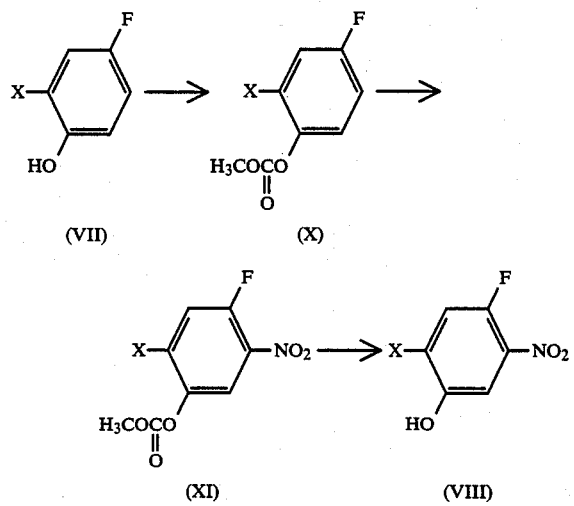

wherein X is as defined above. Thus, the phenol (VII) is converted into its alkali metal salt by treatment with an aqueous solution of an alkali metal hydroxide (e.g. sodium hydroxide, potassium hydroxide), and the resulting salt is reacted with an alkyl haloformate such as methyl chloroformate in water at a temperature of 0° to 10° C. The thus prepared carbonic ester (X) is nitrated with a mixture of conc. sulfuric acid and conc. nitric acid at room temperature. Then, the nitrobenzene (XI) thus obtained is hydrolyzed with an aqueous alkaline solution such as an aqueous sodium hydroxide solution at a temperature of 20° to 120° C. to give the nitrophenol (VIII).

Conversion of the nitrophenol (VIII) into the aminophenol (IX) may be accomplished by any conventional reduction procedure for changing a nitro group to an amino group. Examples of such a reduction procedure are catalytic reduction, reduction with iron powder, reduction with sodium sulfide, reduction with sulfurated sodium borohydride, etc. For instance, treatment of one molar amount of the nitrophenol (VIII) with a 3 molar amount of hydrogen in the presence of a 1/10 to 1/100 molar amount of platinum dioxide in an inert solvent (e.g. ethanol, ethyl acetate) at room temperature under atmospheric pressure affords the aminophenol (IX). Further, for instance, treatment of one molar amount of the nitrophenol (VIII) with a 2 to 5 molar amount of iron powder such as reductive iron or electrolytic iron in a 5% acetic acid solution or a dilute hydrochloric acid solution at a temperature of 80° to 100° C. for a period of 1 to 5 hours produces the aminophenol (IX).

For production of the hydroxyphenyltetrahydrophthalimide (II') from the aminophenol (IX), the latter is reacted with 3,4,5,6-tetrahydrophthalic anhydride in an inert solvent (e.g. acetic acid) while refluxing for a period of 1 to 6 hours, preferably of 2 to 4 hours.

In any event, the phenol (VI) is known (cf. Finger et al.: J.Am.Chem.Soc. 81, 94 (1959)).

Practical and presently preferred embodiments for production of the tetrahydrophthalimides (I) as well as the intermediary compounds are illustratively shown in the following Examples.

Example 1

2-(4-Chloro-2-fluoro-5-hydroxyphenyl)-4,5,6,7-tetrahydro-2H-isoindole-1,3-dione (3 g) is dissolved in dimethylformamide (100 ml), and anhydrous potassium carbonate (0.8 g) is added thereto. To the resultant mixture is added methyl bromoacetate (1.8 g), and the mixture is heated at 70°-80° C. for 3 hours. After being allowed to cool, water is added to the mixture, which is then extracted with ether, and the extract is washed with water, dried and concentrated. The residue is purified by silica gel column chromatography to give 1.3 g of 2-(4-chloro-2-fluoro-5-methoxycarbonylmethoxyphenyl)-4,5,6,7-tetrahydro-2H-isoindole-1,3-dione (Compound No. 1). M.P., 98°-99.5° C.

Example 2

2-(3-Amino-4-bromo-6-fluorophenyl)-4,5,6,7-tetrahydro-2H-isoindole-1,3-dione (0.85 g) is dissolved in 1,4-dioxane (5 ml), and ethyl bromoacetate (3.3 g) is added thereto. The resultant mixture is refluxed for 6 hours. Triethylamine (0.2 g) is added thereto, and the mixture is refluxed for 1 hour. After being allowed to cool, water and toluene are added to the mixture, which is then extracted with toluene. The toluene layer is dried and concentrated. The residue is purified by silica gel column chromatography to give 1.0 g of 2-(4-bromo-2-fluoro-5-ethoxycarbonylmethylaminophenyl)-4,5,6,7-(tetrahydro-2H-isoindole-1,3-dione (Compound No. 89). $n_D^{26.0}$ 1.5281.

Examples of the tetrahydrophthalimides (I) produced by the same procedure as above are shown in Table 1.

TABLE 1

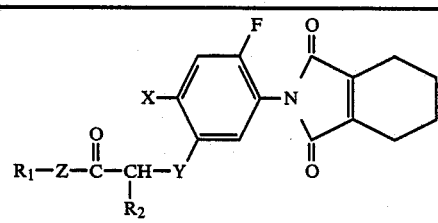

| Compound No. | X | Y | Z | R₁ | R₂ | Physical constant |
|---|---|---|---|---|---|---|
| 1 | Cl | O | O | —CH₃ | H | M.P. 98–99.5° C. |
| 2 | Cl | O | O | —CH₂CH₃ | H | $n_D^{21.5}$ 1.5441 |
| 3 | Cl | O | O | —CH₂CH₂CH₃ | H | $n_D^{14.5}$ 1.5414 |

TABLE 1-continued

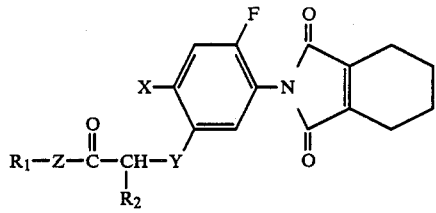
(I)

| Compound No. | X | Y | Z | R₁ | R₂ | Physical constant |
|---|---|---|---|---|---|---|
| 4 | Cl | O | O | —CH(CH₃)₂ | H | $n_D^{14.5}$ 1.5413 |
| 5 | Cl | O | O | —(CH₂)₃CH₃ | H | M.P. 70–73° C. |
| 6 | Cl | O | O | —CH(CH₃)CH₂CH₃ | H | $n_D^{21.5}$ 1.5351 |
| 7 | Cl | O | O | —C(CH₃)₃ | H | $n_D^{14.5}$ 1.5376 |
| 8 | Cl | O | O | —(CH₂)₄CH₃ | H | M.P. 90–91° C. |
| 9 | Cl | O | O | —CH(CH₂CH₃)₂ | H | $n_D^{18}$ 1.5321 |
| 10 | Cl | O | O | —(CH₂)₅CH₃ | H | $n_D^{26}$ 1.5321 |
| 11 | Cl | O | O | —(CH₂)₁₁CH₃ | H | $n_D^{22.5}$ 1.5176 |
| 12 | Cl | O | O | cyclobutyl | H | $n_D^{16}$ 1.5431 |
| 13 | Cl | O | O | cyclopentyl | H | M.P. 100–101° C. |
| 14 | Cl | O | O | cyclohexyl | H | $n_D^{17.0}$ 1.5619 |
| 15 | Cl | O | O | 4-methylcyclohexyl | H | $n_D^{18}$ 1.5378 |
| 16 | Cl | O | O | 3-methylcyclohexyl | H | $n_D^{18}$ 1.5401 |
| 17 | Cl | O | O | 2-methylcyclohexyl | H | $n_D^{16.5}$ 1.5345 |

TABLE 1-continued

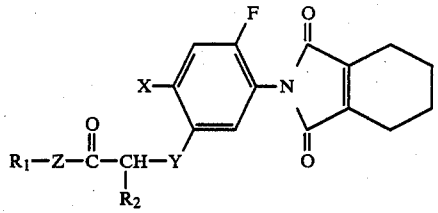

(I)

| Compound No. | X | Y | Z | $R_1$ | $R_2$ | Physical constant |
|---|---|---|---|---|---|---|
| 18 | Cl | O | O | cycloheptyl | H | $n_D^{14.0}$ 1.5439 |
| 19 | Cl | O | O | —CH$_2$-cyclopropyl | H | $n_D^{15.0}$ 1.5513 |
| 20 | Cl | O | O | —CH$_2$-cyclopentyl | H | $n_D^{15.5}$ 1.5418 |
| 21 | Cl | O | O | —CH$_2$CH$_2$OCH$_3$ | H | $n_D^{20}$ 1.5440 |
| 22 | Cl | O | O | —CH$_2$CH$_2$OCH$_2$CH$_3$ | H | $n_D^{19}$ 1.5275 |
| 23 | Cl | O | O | —CH$_2$CH$_2$OCH$_2$CH$_2$CH$_3$ | H | $n_D^{21.5}$ 1.5358 |
| 24 | Cl | O | O | —CH(CH$_3$)CH$_2$OCH$_3$ | H | $n_D^{19}$ 1.5402 |
| 25 | Cl | O | O | —CH$_2$CH$_2$CH$_2$OCH$_3$ | H | $n_D^{21.5}$ 1.5429 |
| 26 | Cl | O | O | —CH$_2$CH$_2$CH(CH$_3$)OCH$_3$ | H | M.P. 102–103° C. |
| 27 | Cl | O | O | —CH$_2$CH$_2$SCH$_2$CH$_3$ | H | $n_D^{18}$ 1.5395 |
| 28 | Cl | O | O | —CH$_2$CH$_2$CN | H | $n_D^{20}$ 1.5507 |
| 29 | Cl | O | O | —CH$_2$CH$_2$F | H | $n_D^{20.5}$ 1.5476 |
| 30 | Cl | O | O | —CH$_2$CH$_2$Cl | H | $n_D^{15}$ 1.5496 |
| 31 | Cl | O | O | —CH$_2$CHCl$_2$ | H | M.P. 105–107° C. |
| 32 | Cl | O | O | —CH$_2$CF$_3$ | H | $n_D^{15}$ 1.5205 |
| 33 | Cl | O | O | —CH$_2$CH$_2$CH$_2$Cl | H | M.P. 71–72° C. |
| 34 | Cl | O | O | —CH(CH$_2$F)(CH$_2$F) | H | $n_D^{20.5}$ 1.5490 |
| 35 | Cl | O | O | —CH(CF$_3$)(CF$_3$) | H | M.P. 82–84.5° C. |
| 36 | Cl | O | O | —CH(CH$_3$)(CCl$_3$) | H | $n_D^{22.5}$ 1.5597 |
| 37 | Cl | O | O | —CH$_2$CH(Cl)CH$_2$Cl | H | $n_D^{23.5}$ 1.5500 |
| 38 | Cl | O | O | —CH$_2$CF$_2$CF$_2$H | H | $n_D^{24}$ 1.5156 |
| 39 | Cl | O | O | —CH$_2$CH$_2$CH$_2$CH$_2$Cl | H | M.P. 80–82.5° C. |
| 40 | Cl | O | O | —CH$_2$CH$_2$Br | H | $n_D^{15.5}$ 1.5611 |
| 41 | Cl | O | O | —CH$_2$CH=CH$_2$ | H | $n_D^{16}$ 1.5615 |

TABLE 1-continued
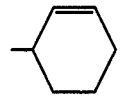
(I)
| Compound No. | X | Y | Z | R₁ | R₂ | Physical constant |
|---|---|---|---|---|---|---|
| 42 | Cl | O | O | 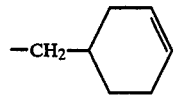 | H | $n_D^{17}$ 1.5412 |
| 43 | Cl | O | O | 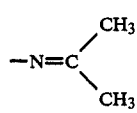 | H | $n_D^{17.5}$ 1.5345 |
| 44 | Cl | O | O | 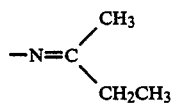 | H | $n_D^{23.5}$ 1.5572 |
| 45 | Cl | O | O | 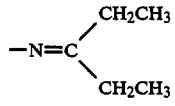 | H | $n_D^{18}$ 1.5470 |
| 46 | Cl | O | O | 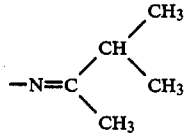 | H | $n_D^{16.5}$ 1.5568 |
| 47 | Cl | O | O | 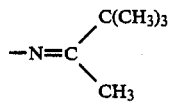 | H | $n_D^{16}$ 1.5421 |
| 48 | Cl | O | O | 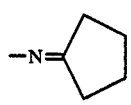 | H | $n_D^{17.5}$ 1.5589 |
| 49 | Cl | O | O | 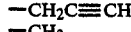 | H | $n_D^{16.0}$ 1.5707 |
| 50 | Cl | O | O | —CH₂C≡CH | H | M.P. 91–91.5° C. |
| 51 | Cl | O | O | —CH₃ | —CH₃ | M.P. 57.1° C. |
| 52 | Cl | O | O | —CH₂CH₃ | —CH₃ | $n_D^{21.0}$ 1.5399 |
| 53 | Cl | O | O | —CH₂CH₂CH₂Cl | —CH₃ | M.P. 60–64° C. |
| 54 | Cl | O | O | —(CH₂)₄CH₃ | —CH₃ | $n_D^{26}$ 1.5241 |
| 55 | Cl | O | O | 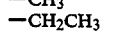 | —CH₃ | M.P. 108–113° C. |
| 56 | Cl | O | O | —CH₂CH₃ | —CH₂CH₂CH₃ | $n_D^{21.0}$ 1.5254 |
| 57 | Cl | O | O | —CH₃ | —OCH₃ | $n_D^{24}$ 1.5391 |
| 58 | Cl | O | O | 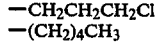 | —OCH₃ | $n_D^{24.5}$ 1.5268 |

TABLE 1-continued

(I)

| Compound No. | X | Y | Z | $R_1$ | $R_2$ | Physical constant |
|---|---|---|---|---|---|---|
| 59 | Cl | O | O | —(CH$_2$)$_4$CH$_3$ | —OCH$_3$ | $n_D^{25.0}$ 1.5294 |
| 60 | Cl | O | O |  | —OCH$_3$ | $n_D^{27.5}$ 1.5401 |
| 61 | Cl | O | O |  | —OCH$_3$ | $n_D^{24.5}$ 1.5272 |
| 62 | Br | O | O | —(CH$_2$)$_3$CH$_3$ | H | $n_D^{23.5}$ 1.5376 |
| 63 | Br | O | O | 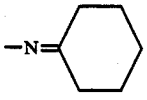 | H | $n_D^{19}$ 1.5448 |
| 64 | Br | O | O | —CH$_2$CH$_2$OCH$_3$ | H | $n_D^{20}$ 1.5475 |
| 65 | Br | O | O | —CH$_2$CH$_2$Cl | H | $n_D^{17.0}$ 1.5593 |
| 66 | Br | O | O | 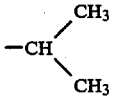 | H | $n_D^{18}$ 1.5504 |
| 67 | Cl | O | S | —CH$_2$CH$_3$ | H | M.P. 116–119° C. |
| 68 | Cl | O | S | —CH(CH$_3$)$_2$ | H | $n_D^{26}$ 1.5531 |
| 69 | Cl | O | S | —CH$_2$CH$_2$CH$_2$CH$_3$ | H | M.P. 82–84° C. |
| 70 | Cl | O | S | —CH$_2$CH$_2$CH$_2$CH$_2$CH$_2$CH$_3$ | H | M.P. 97–100° C. |
| 71 | Cl | O | S |  | H | M.P. 127–129° C. |
| 72 | Cl | O | S | —CH$_2$CH=CH$_2$ | H | M.P. 145–147° C. |
| 73 | Cl | O | S |  | H | $n_D^{24}$ 1.5811 |
| 74 | Cl | O | S | 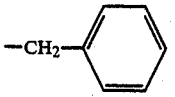 | H | M.P. 147–150° C. |
| 75 | Cl | O | S | —CH$_2$CH$_2$CH$_2$CH$_2$CH$_3$ | —CH$_3$ | $n_D^{25}$ 1.5314 |
| 76 | Cl | O | S | —CH$_2$CH$_2$CH$_3$ | —C$_3$H$_7$(n) | $n_D^{25.5}$ 1.5319 |
| 77 | Br | O | S | —CH$_2$CH$_2$CH$_2$CH$_2$CH$_3$ | H | M.P. 81–84° C. |
| 78 | Cl | —NH— | O | —CH$_2$CH$_3$ | H | $n_D^{28}$ 1.5519 |

TABLE 1-continued (I) Structure: a phenyl ring with F (ortho), N-tetrahydrophthalimide group, X para to F, and an -O-CH(R₂)-C(=O)-Z-R₁ group meta.

| Compound No. | X | Y | Z | R₁ | R₂ | Physical constant |
|---|---|---|---|---|---|---|
| 79 | Cl | —NH— | O | —CH(CH₃)CH₂CH₃ | H | $n_D^{24.5}$ 1.5445 |
| 80 | Cl | —NH— | O | —CH(CH₂CH₃)₂ | H | $n_D^{25}$ 1.5401 |
| 81 | Cl | —NH— | O | cyclopentyl | H | Glassy |
| 82 | Cl | —NH— | O | —CH₂-cyclopentyl | H | $n_D^{25}$ 1.5466 |
| 83 | Cl | —NH— | O | —CH₂CHCl₂ | H | Glassy |
| 84 | Cl | —NH— | O | —CH₂CH(Cl)CH₂Cl | H | M.P. 119–120° C. |
| 85 | Cl | —NH— | O | —CH₂CH₂OCH₂CH₂CH₃ | H | $n_D^{25}$ 1.5364 |
| 86 | Cl | —NH— | O | —CH₂CH₂CN | H | $n_D^{25}$ 1.5541 |
| 87 | Cl | —NH— | S | —CH₂CH₂CH₂CH₂CH₃ | H | $n_D^{24}$ 1.5621 |
| 88 | Cl | —NH— | O | —CH₃ | —CH₃ | Glassy |
| 89 | Br | —NH— | O | —CH₂CH₃ | H | $n_D^{26}$ 1.5281 |
| 90 | Br | —NH— | O | —CH₂CH₂OCH₃ | H | M.P. 106–107° C. |
| 91 | Br | —NH— | O | —CH₃ | —CH₃ | $n_D^{24.5}$ 1.5661 |
| 92 | Br | —NH— | O | cyclopentyl | —OCH₃ | $n_D^{24.5}$ 1.5596 |
| 93 | Cl | O | S | —CH₂CH₂CH₂CH₂CH₃ | H | M.P. 87–88° C. |
| 94 | Cl | O | O | H | H | M.P. 148.5–150° C. |

EXAMPLE 3

Production of the HY-phenyltetrahydrophthalimide (II: X=Cl; Y=NH):

A solution of N-(4-chloro-2-fluoro-5-nitrophenyl)-3,4,5,6-tetrahydrophthalimide (16.2 g) in acetic acid (200 ml) is dropwise added to a suspension of iron powder (14 g) in a 5% aqueous acetic acid (30 ml) at 90°–100° C. and refluxed for 1 hour. After being allowed to cool, chloroform is added to the resultant mixture, followed by filtration. The organic layer is separated from the filtrate, washed with a saturated sodium hydrogen carbonate solution, dried and concentrated. The residue is recrystallized from a mixture of ether and petroleum ether to give 7.5 g of N-(3-amino-4-chloro-6-fluorophenyl)-3,4,5,6-tetrahydrophthalimide. M.P., 144.5°–146.5° C.

EXAMPLE 4

Production of the HY-phenyltetrahydrophthalimide (II: X=Br; Y=NH):

In the same manner as in Example 3 but using N-(4-bromo-2-fluoro-5-nitrophenyl)-3,4,5,6-tetrahydrophthalimide in place of N-(4-chloro-2-fluoro-5-nitrophenyl)-3,4,5,6-tetrahydrophthalimide, there is produced N-(3-amino-4-bromo-6-fluorophenyl)-3,4,5,6-tetrahydrophthalimide. M.P., 163°–164.5° C.

Example 5

Production of the HY-phenyltetrahydrophthalimide (II: X=Cl; Y=O):

2-Chloro-4-fluoro-5-aminophenol (6.6 g) and 2,4,5,6-tetrahydrophthalic anhydride (6 g) are dissolved in acetic acid (20 ml) and refluxed for 2 hours. The resultant mixture is allowed to cool to room temperature and poured into ice-water, followed by extraction with ether. The ether extract is washed with a saturated sodium hydrogen carbonate solution and water in order, dried over anhydrous magnesium sulfate and concentrated. The residue is purified by silica gel chromatography to give 4.0 g of N-(4-chloro-2-fluoro-5-hydroxyphenyl)-3,4,5,6-tetrahydrophthalimide. M.P., 151° C.

NMR (CDCl$_3$, D$_6$DMSO) Γ (ppm): 1.5-2.0 (4H, m), 2.1-2.6 (4H, m), 6.8 (1H, d, J=6 Hz), 7.15 (1H, d, J=10 Hz).

IR $\nu_{max}^{nujol}$ (cm$^{-1}$): 3380, 1680.

Example 6

Production of the HY-phenyltetrahydrophthalimide (II: X=Br; Y=O):

In the same manner as in Example 5 but using 2-bromo-4-fluoro-5-aminophenol in place of 2-chloro-4-fluoro-5-aminophenol, there is produced N-(4-bromo-2-fluoro-5-hydroxyphenyl)-3,4,5,6-tetrahydrophthalimide. M.P., 167°-168° C.

NMR (CDCl$_3$, D$_6$-DMSO) δ (ppm): 1.5-2.0 (4H, m), 2.1-2.7 (4H, m), 6.8 (1H, d, J=6 Hz), 7.25 (1H, d, J=10 Hz). IR $\nu_{max}^{nujol}$ (cm$^{-1}$): 3380, 1690.

Example 7

Production of the nitrophenyltetrahydrophthalimide (IV: X=Cl):

4-Chloro-2-fluoro-5-nitroaniline (19 g) and 3,4,5,6-tetrahydrophthalic anhydride (15.2 g) are dissolved in acetic acid (50 ml) and refluxed for 6 hours. After being allowed to cool, the resultant mixture is poured into water and extracted with toluene. The toluene layer is washed with water, an aqueous sodium hydrogen carbonate solution and water in order, dried and concentrated. The residue is crystallized from ethanol to give 20 g of N-(4-chloro-2-fluoro-5-nitrophenyl)-3,4,5,6-tetrahydrophthalimide. M.P., 157°-157.5° C.

Example 8

Production of the nitrophenyltetrahydrophthalimide (IV: X=Br):

In the same manner as in Example 7 but using 4-bromo-2-fluoro-5-nitroaniline in place of 4-chloro-2-fluoro-5-nitroaniline, there is produced N-(4-bromo-2-fluoro-5-nitrophenyl)-3,4,5,6-tetrahydrophthalimide. M.P., 155°-156° C.

Example 9

Production of the nitroaniline (VI: X=Br):

To a solution of 4-bromo-2-fluoroaniline (58.6 g) in conc. sulfuric acid (100 ml), there is dropwise added a mixture of conc. nitric acid (25.3 g) and conc. sulfuric acid (15 ml) at a temperature of 0° to −10° C. The resultant mixture is stirred at 0°-5° C. for 1 hour, poured into ice-water and extracted with toluene. The toluene layer is washed with water and an aqueous sodium hydrogen carbonate solution and concentrated. The residue is purified by silica gel chromatography to give 16.4 g of 4-bromo-2-fluoro-5-nitroaniline. M.P., 90°-92° C.

Example 10

Production of the nitroaniline (VI: X=Cl):

In the same manner as in Example 9 but using 4-chloro-2-fluoroaniline in place of 4-bromo-2-fluoroaniline, there is produced 4-chloro-2-fluoro-5-nitroaniline. M.P., 83°-84.5° C.

Example 11

Production of the nitrophenol (VII: X=Cl):

2-Chloro-4-fluorophenol (83.4 g) is added to a solution of sodium hydroxide (27.7 g) in water (450 ml), and methyl chloroformate (69.2 g) is dropwise added thereto at a temperature below 10° C. Precipitated crystals are collected by filtration and washed with water to give methyl (2-chloro-4-fluorophenyl)formate (134.8 g). M.P., 69°-71° C.

Methyl (2-chloro-4-fluorophenyl)formate (134.8 g) obtained above is suspended in conc. sulfuric acid (50 ml). To the suspension, a mixture of conc. sulfuric acid (50 ml) and conc. nitric acid (50 ml) is added at about 30° C., and the mixture is stirred for 1 hour at this temperature. The reaction mixture is poured into ice-water, and precipitated crystals are collected and washed with water. Methyl (2-chloro-4-fluoro-4-nitrophenyl)formate (143 g) is thus obtained. M.P., 53°-55° C.

The product obtained as above is combined with sodium hydroxide (27 g) and water (300 ml), and the resultant mixture is refluxed for 4 hours. Precipitated insoluble materials are filtered using a celite, and the filtrate is acidified with conc. hydrochloric acid. Precipitated crystals are collected by filtration and washed with water to obtain 76.3 g of 2-chloro-4-fluoro-5-nitrophenol. M.P. 106°-107° C.

NMR (CDCl$_3$, D$_6$-DMSO) δ (ppm): 7.25 (1H, d, J=10 Hz), 7.64 (1H, d, J=6 Hz).

IR $\nu_{max}^{nujol}$ (cm$^{-1}$): 3370.

Example 12

Production of the nitrophenol (VII: X=Br):

2-Bromo-4-fluorophenol (28 g) is added to a solution of sodium hydroxide (7 g) in water (100 ml), and methyl chloroformate is dropwise added thereto at a temperature below 10° C. Precipitated crystals are collected by filtration and washed with water to give methyl (2-bromo-4-fluorophenyl)formate (41 g). M.P., 80.7° C.

The thus obtained methyl (2-bromo-4-fluorophenyl)formate is suspended in conc. sulfuric acid (13 ml). To the suspension, a mixture of conc. sulfuric acid (13 ml) and conc. nitric acid (13 ml) is added at about 30° C. The mixture is stirred for 30 minutes and poured onto ice. Precipitated crystals are thoroughly washed with water, whereby yellow crystals of methyl (2-bromo-4-fluoro-5-nitrophenyl)formate (38.3 g) are obtained. M.P., 63.5°-64.5° C.

The product thus obtained is refluxed together with sodium hydroxide (6.2 g) and water (100 ml) for 3 hours. Insoluble materials are filtered, and the filtrate is acidified with hydrochloric acid. Precipitated crystals are collected by filtration and washed with water to obtain 25 g of 2-bromo-4-fluoro-5-nitrophenol. M.P., 126°-127° C.

NMR (CDCl$_3$, D$_6$-DMSO) δ (ppm): 7.42 (1H, d, J=10 Hz), 7.65 (1H, d, J=6 Hz).

IR $\nu_{max}^{nujol}$ (cm$^{-1}$): 3450.

Example 13

Production of the aminophenol (IX: C=Cl):

A suspension of 2-chloro-4-fluoro-5-nitrophenol (9.17 g) and platinum dioxide (500 mg) in ethanol (120 ml) is subjected to catalytic reduction with hydrogen at room temperature and atmospheric pressure until a designed amount of hydrogen is absorbed. The catalyst is removed by filtration, and the filtrate is concentrated. The residue is extracted with ether, and the ether layer is concentrated to obtain 6.6 g of 3-amino-6-chloro-4-fluorophenol. M.P., 145°–146° C. (decomp.).

NMR (CDCl$_3$, D$_6$-DMSO) δ (ppm): 6.4 (1H, d, J=8 Hz), 6.85 (1H, d, J=11 Hz).

IR $\nu_{max}^{nujol}$ (cm$^{-1}$): 3400, 3320.

Example 14

Production of the aminophenol (IX: X=Br):

In the same manner as above but using 2-bromo-4-fluoro-5-nitrophenol in place of 2-chloro-4-fluoro-5-nitrophenol, there is produced 3-amino-6-bromo-4-fluorophenol. M.P., 129°–130.5° C. (decomp.).

NMR (CDCl$_3$, D$_6$-DMSO) δ (ppm): 6.57 (1H, d, J=8 Hz), 7.1 (1H, d, J=11 Hz).

IR $\nu_{max}^{nujol}$ (cm$^{-1}$): 3400, 3320.

In the practical usage of the tetrahydrophthalimides (I), these tetrahydrophthalimides may be applied in any composition form such as emulsifiable concentrates, wettable powders, suspensions, granules or dusts.

The concentration of the active ingredient in such composition is usually within a range of 0.1 to 95% by weight, preferably of 1 to 80% by weight.

In the formulation of these compositions, a solid or liquid carrier or a diluent may be used. As the solid carrier or the diluent, there may be employed fine dust or granules of kaolin clay, attapulgite clay, bentonite, terra alba, pyrophyllite, talc, diatomaceous earth, calcite, walnut powder, urea, ammonium sulfate, synthetic hydrated silicon dioxide, etc. As the liquid carrier or the diluent, there may be employed aromatic hydrocarbons (e.g. xylene, methylnaphthalene), alcohols (e.g. isopropanol, ethylene glycol, cellosolve), ketones (e.g. acetone, cyclohexanone, isophorone), plant oils (e.g. soybean oil, cottonseed oil), dimethylsulfoxide, acetonitrile, water, etc.

A surface active agent used for emulsification, dispersion or spreading may be any of the non-ionic, anionic, cationic and amphoteric type of agents. Examples of the surface active agent include alkylsulfates, alkylaryl sulfonates, dialkylsuccinates, polyoxyethylene alkylaryl phosphates, polyoxyethylene alkyl ethers, polyoxyethylene alkylaryl ethers, polyoxyethylene-polyoxypropylene blocked polymers, sorbitan fatty acid esters, polyoxyethylene sorbitan fatty acid esters, polyoxyethylene resin acid esters, abietic acid, dinaphthylmethanedisulfonates, paraffin and the like. If necessary, ligninsulfonates, alginates, polyvinyl alcohol, gum arabic, CMC (carboxymethylcellulose), PAP (isopropyl acid phosphate) or the like may be used as an auxiliary agent.

Practical embodiments of the herbicidal composition according to the invention are illustratively shown in the following examples wherein part(s) and % are by weight. The compound number of the active ingredient corresponds to those shown in Table 1.

Formulation Example 1

Eighty parts of Compound No. 1, 12, 26, 35 or 47, 5 parts of polyoxyethylene alkylaryl ether and 15 parts of synthetic hydrated silicon dioxide are well mixed while being powdered to obtain a wettable powder.

Formulation Example 2

Ten parts of Compound No. 2, 8, 14, 22, 32 or 45, 7 parts of polyoxyethylene alkylaryl ether, 3 parts of alkylarylsulfonate and 80 parts of cyclohexanone are well mixed while being powdered to obtain an emulsifiable concentrate.

Formulation Example 3

One part of Compound No. 1, 12, 23, 26, 35 or 44, 1 part of synthetic hydrated silicon dioxide, 5 parts of ligninsulfonate and 93 parts of kaolin clay are well mixed while being powdered. The mixture is then kneaded with water, granulated and dried to obtain a granule.

Formulation Example 4

Three parts of Compound No. 1, 30, 31, 44 or 63, 0.5 part of isopropyl acid phosphate, 66.5 parts of kaolin clay and 30 parts of talc are well mixed while being powdered to obtain a dust.

Formulation Example 5

Twenty parts of Compound No. 2, 13, 17, 25, 33 or 47 is mixed with 60 parts of an aqueous solution containing 3% of polyoxyethylene sorbitan monooleate and pulverized until the particle size of the active ingredient becomes less than 3 microns. Twenty parts of an aqueous solution containing 3% of sodium alginate as a dispersing agent is incorporated therein to obtain a suspension.

Formulation Example 6

Fifty parts of Compound No. 67 or 84, 3 parts of calcium ligninsulfonate, 2 parts of sodium laurylsulfate and 45 parts of synthetic hydrated silicon dioxide are well mixed while being powdered to obtain a wettable powder.

Formulation Example 7

Ten parts of Compound No. 68 or 81, 14 parts of polyoxyethylene styrylphenyl ether, 6 parts of calcium dodecylbenzenesulfonate, 30 parts of xylene and 40 parts of cyclohexanone are well mixed while being powdered to obtain an emulsifiable concentrate.

Formulation Example 8

Two parts of Compound No. 75 or 85, 1 part of synthetic hydrated silicon doxode, 2 parts of calcium ligninsulfonate, 30 parts of bentonite and 65 parts of kaolin clay are well mixed while being powdered. The mixture is then kneaded with water, granulated and dried to obtain a granule.

Formulation Example 9

Twenty-five parts of Compound No. 71 or 84, 3 parts of polyoxyethylene sorbitan monooleate, 3 parts of carboxymethyl cellulose and 69 parts of water are well mixed and pulverized until the particle size of the active ingredient becomes less than 5 microns to obtain a granule.

These compositions comprising the tetrahydrophthalimides (I) may be applied as such, or after dilution with water, to the weeds in suitable application modes such as spraying, perfusion, etc. For instance, they may be spead over, perfused into or admixed with soil. Further, for instance, they may be applied for foliar treatment. If necessary, they may be used together with other herbicides to improve their activity as herbicides, and in some cases, a synergistic effect can be expected. They may also be applied in combination with insecticides, acaricides, nematocides, fungicides, plant growth regulators, fertilizers, soil controlling agents, etc.

The dosage rate of the tetrahydrophthalimide (I) as the active ingredient may be generally from 0.01 to 100 grams, preferably from 0.1 to 50 grams, per are. In the practical usage of the tetrahydrophthalimide (I) as emulsifiable concentrates, wettable powders or suspensions, it may be diluted with 1 to 10 liters of water (optionally including an auxiliary agent such as a spreading agent) per are. When formulated into granules or dust, it may be used as such without dilution.

The application of the tetrahydrophthalimides (I) as herbicides will be illustratively shown in the following Examples wherein the phytotoxicity to cultivated plants and the herbicidal activity on weeds are evaluated as follows: the aerial parts of the test plants are cut off and weighed (fresh weight); the percentage of the fresh weight of the treated plant to that of the untreated plant is calculated with the latter fresh weight taken as 100; and the phytotoxicity and the herbicidal activity are evaluated by the standard given in the table below.

| Rating value | Fresh weight (percentage to untreated plot) (%) | |
|---|---|---|
| | Herbicidal activity | Phytotoxicity |
| 0 | 91– | 91– |
| 1 | 71–90 | 71–90 |
| 2 | 41–70 | 51–70 |
| 3 | 11–40 | 31–50 |
| 4 | 1–10 | 11–30 |
| 5 | 0 | 0–10 |

The following compounds are used in the Examples for comparison:

| Compound No. | Structure | Remarks |
|---|---|---|
| (a) | [2-fluoro-4-chlorophenyl tetrahydrophthalimide structure] | U.S. Pat. No. 4,032,326 |
| (b) | [4-chlorophenyl tetrahydrophthalimide structure] | U.S. Pat. No. 3,984,435 |
| (c) | [substituted phenyl tetrahydrophthalimide with (n)H$_7$C$_3$—S—C(=O)—CH(C$_3$H$_7$(n))—CHO group] | EP 0049508A |
| (d) | [2,4,5-trichlorophenoxy — OCH$_2$COONa] | Commercially available herbicide known as "2,4,5-T" (Na salt) |
| (e) | [Bentazone structure with N—CH(CH$_3$)$_2$, SO$_2$, N—Na] | Commercially available herbicide known as "Bentazone" (Na salt) |
| (f) | [triazine with Cl, (CH$_3$)$_2$HCHN, NHC$_2$H$_5$] | Commercially available herbicide known as "Atrazine" |

-continued

| Compound No. | Structure | Remarks |
|---|---|---|
| (g) | 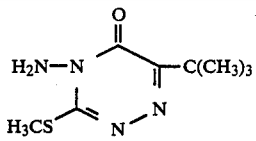 | Commercially available herbicide known as "Metribuzin" |
| (h) | 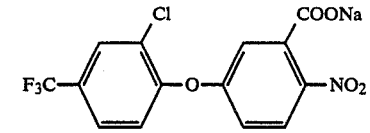 | Commercially available herbicide known as "Acifluorfensodium" |

Test Example 1

Trays (33×23 cm$^2$) are filled with upland field soil, and the seeds of soybean, tall morningglory, velvet-leaf, black nightshade, cocklebur and hemp sesbania are sowed therein and grown for 18 days in a greenhouse. A designed amount of the test compound formulated into an emulsifiable concentrate and diluted with water was sprayed to the foliage of the test plants over the top by means of a small hand sprayer at a spray volume of 10 liters per are. At the time of application, the test plants are generally at the 2 to 4 leaf stage and had a height of 2 to 12 cm. Twenty days thereafter, herbicidal activity and phytotoxicity are examined. The results are shown in Table 2.

TABLE 2

| Compound No. | Dosage (weight of active ingredient, g/are) | Phytotoxicity Soybean | Herbicidal activity | | | | |
|---|---|---|---|---|---|---|---|
| | | | Tall morningglory | Velvetleaf | Black nightshade | Cocklebur | Hemp sesbania |
| 1 | 0.4 | 1 | 5 | 5 | 5 | 5 | 5 |
| | 0.2 | 0 | 5 | 5 | 5 | 5 | 5 |
| 2 | 0.4 | 0 | 5 | 5 | 5 | 5 | 5 |
| | 0.2 | 0 | 5 | 5 | 5 | 5 | 5 |
| 3 | 0.4 | 1 | 5 | 5 | 5 | 5 | 5 |
| | 0.2 | 0 | 5 | 5 | 5 | 5 | 5 |
| 4 | 0.4 | 0 | 5 | 5 | 5 | 5 | 5 |
| | 0.2 | 0 | 5 | 5 | 5 | 5 | 5 |
| 5 | 0.4 | 0 | 5 | 5 | 5 | 5 | 5 |
| | 0.2 | 0 | 5 | 5 | 5 | 5 | 5 |
| 6 | 0.4 | 1 | 5 | 5 | 5 | 5 | 5 |
| | 0.2 | 0 | 5 | 5 | 5 | 5 | 5 |
| 7 | 0.4 | 1 | 5 | 5 | 5 | 5 | 5 |
| | 0.2 | 0 | 5 | 5 | 5 | 5 | 5 |
| 8 | 0.4 | 0 | 5 | 5 | 5 | 5 | 5 |
| | 0.2 | 0 | 5 | 5 | 5 | 4 | 5 |
| 9 | 0.8 | 1 | 5 | 5 | 5 | 5 | 5 |
| | 0.4 | 0 | 5 | 5 | 5 | 5 | 5 |
| 10 | 0.4 | 0 | 5 | 5 | 5 | 5 | 5 |
| | 0.2 | 0 | 5 | 5 | 5 | 5 | 5 |
| 11 | 0.8 | 0 | 5 | 5 | 5 | 5 | 5 |
| | 0.4 | 0 | 5 | 5 | 5 | 4 | 4 |
| 12 | 0.4 | 1 | 5 | 5 | 5 | 5 | 5 |
| | 0.2 | 0 | 5 | 5 | 5 | 4 | 5 |
| 13 | 0.4 | 0 | 5 | 5 | 5 | 5 | 5 |
| | 0.2 | 0 | 5 | 5 | 5 | 5 | 5 |
| 14 | 0.4 | 0 | 5 | 5 | 5 | 5 | 5 |
| | 0.2 | 0 | 4 | 5 | 5 | 4 | 5 |
| 15 | 0.4 | 1 | 5 | 5 | 5 | 5 | 5 |
| | 0.2 | 1 | 5 | 5 | 5 | 5 | 5 |
| 16 | 0.4 | 1 | 5 | 5 | 5 | 5 | 5 |
| | 0.2 | 1 | 5 | 5 | 5 | 5 | 5 |
| 17 | 0.4 | — | 5 | 5 | 5 | 5 | 5 |
| | 0.2 | 1 | 4 | 5 | 5 | 5 | 4 |
| 18 | 0.4 | 1 | 5 | 5 | 5 | 5 | 5 |
| | 0.2 | 0 | 5 | 5 | 5 | 5 | 5 |
| 19 | 0.4 | 1 | 5 | 5 | 5 | 5 | 5 |

TABLE 2-continued

| Compound No. | Dosage (weight of active ingredient, g/are) | Phytotoxicity Soybean | Herbicidal activity | | | | |
|---|---|---|---|---|---|---|---|
| | | | Tall morningglory | Velvetleaf | Black nightshade | Cocklebur | Hemp sesbania |
| | 0.2 | 0 | 5 | 5 | 5 | 5 | 5 |
| 20 | 0.4 | 1 | 5 | 5 | 5 | 5 | 5 |
| | 0.2 | 0 | 5 | 5 | 5 | 5 | 5 |
| 21 | 0.4 | 1 | 5 | 5 | 5 | 5 | 5 |
| | 0.2 | 0 | 5 | 5 | 5 | 5 | 5 |
| 22 | 0.4 | 0 | 5 | 5 | 5 | 5 | 5 |
| | 0.2 | 0 | 5 | 5 | 5 | 4 | 5 |
| 23 | 0.4 | 1 | 5 | 5 | 5 | 5 | 5 |
| | 0.2 | 0 | 5 | 5 | 5 | 4 | 5 |
| 24 | 0.4 | 1 | 5 | 5 | 5 | 5 | 5 |
| | 0.2 | 0 | 5 | 5 | 5 | 5 | 5 |
| 25 | 0.4 | 1 | 5 | 5 | 5 | 5 | 5 |
| | 0.2 | 0 | 5 | 5 | 5 | 4 | 4 |
| 26 | 0.4 | 0 | 5 | 5 | 5 | 5 | 5 |
| | 0.2 | 0 | 5 | 5 | 5 | 5 | 5 |
| 27 | 0.4 | 1 | 5 | 5 | 5 | 5 | 5 |
| | 0.2 | 0 | 5 | 5 | 5 | 5 | 5 |
| 28 | 0.4 | 1 | 5 | 5 | 5 | 5 | 5 |
| | 0.2 | 0 | 5 | 5 | 5 | 5 | 5 |
| 29 | 0.63 | 1 | 5 | 5 | 5 | 5 | 5 |
| | 0.16 | 0 | 4 | 5 | 5 | 4 | 5 |
| 30 | 0.63 | 0 | 5 | 5 | 5 | 5 | 5 |
| | 0.16 | 0 | 5 | 5 | 5 | 5 | 5 |
| 31 | 0.63 | 0 | 5 | 5 | 5 | 5 | 5 |
| | 0.16 | 0 | 5 | 5 | 5 | 4 | 5 |
| 32 | 0.63 | 1 | 5 | 5 | 5 | 5 | 5 |
| | 0.16 | 0 | 5 | 5 | 5 | 4 | 4 |
| 33 | 0.63 | 1 | 5 | 5 | 5 | 5 | 5 |
| | 0.16 | 0 | 4 | 5 | 5 | 5 | 5 |
| 34 | 0.63 | — | 5 | 5 | 5 | 5 | 5 |
| | 0.16 | 0 | 4 | 5 | 5 | 4 | 5 |
| 35 | 0.63 | 0 | 5 | 5 | 5 | 5 | 5 |
| | 0.16 | 0 | 4 | 5 | 5 | 4 | 5 |
| 36 | 0.63 | 0 | 5 | 5 | 5 | 5 | 5 |
| | 0.16 | 0 | 5 | 5 | 5 | 4 | 5 |
| 37 | 0.63 | 0 | 5 | 5 | 5 | 5 | 5 |
| | 0.16 | 0 | 5 | 5 | 5 | 5 | 5 |
| 38 | 0.63 | 0 | 5 | 5 | 5 | 5 | 5 |
| | 0.16 | 0 | 5 | 5 | 5 | 4 | 5 |
| 39 | 0.63 | — | 5 | 5 | 5 | 5 | 5 |
| | 0.16 | 0 | 5 | 5 | 5 | 5 | 5 |
| 40 | 0.63 | 1 | 5 | 5 | 5 | 5 | 5 |
| | 0.16 | 0 | 4 | 5 | 5 | 4 | 5 |
| 41 | 0.4 | 1 | 5 | 5 | 5 | 5 | 5 |
| | 0.2 | 0 | 5 | 5 | 5 | 5 | 4 |
| 42 | 0.4 | 1 | 5 | 5 | 5 | 5 | 5 |
| | 0.2 | 0 | 5 | 5 | 5 | 5 | 4 |
| 43 | 0.4 | 1 | 5 | 5 | 5 | 5 | 5 |
| | 0.2 | 0 | 5 | 5 | 5 | 5 | 5 |
| 44 | 0.4 | 1 | 5 | 5 | 5 | 5 | 5 |
| | 0.2 | 0 | 5 | 5 | 5 | 5 | 5 |
| 45 | 0.4 | 0 | 5 | 5 | 5 | 5 | 5 |
| | 0.2 | 0 | 5 | 5 | 5 | 5 | 5 |
| 46 | 0.4 | 1 | 5 | 5 | 5 | 5 | 5 |
| | 0.2 | 1 | 5 | 5 | 5 | 4 | 4 |

TABLE 2-continued

| Compound No. | Dosage (weight of active ingredient, g/are) | Phytotoxicity Soybean | Herbicidal activity | | | | |
|---|---|---|---|---|---|---|---|
| | | | Tall morningglory | Velvetleaf | Black nightshade | Cocklebur | Hemp sesbania |
| 47 | 0.4 | 1 | 5 | 5 | 5 | 5 | 5 |
| | 0.2 | 0 | 5 | 5 | 5 | 5 | 4 |
| 48 | 0.4 | — | 5 | 5 | 5 | 5 | 5 |
| | 0.2 | 1 | 5 | 5 | 5 | 5 | 5 |
| 49 | 0.4 | 1 | 5 | 5 | 5 | 5 | 5 |
| | 0.2 | 0 | 5 | 5 | 5 | 4 | 5 |
| 50 | 0.4 | 1 | 5 | 5 | 5 | 5 | 5 |
| | 0.2 | 0 | 5 | 5 | 5 | 5 | 5 |
| 51 | 0.4 | 1 | 5 | 5 | 5 | 5 | 5 |
| | 0.2 | 1 | 5 | 5 | 5 | 5 | 5 |
| 52 | 0.4 | — | 5 | 5 | 5 | 5 | 5 |
| | 0.2 | 1 | 5 | 5 | 5 | 5 | 5 |
| 53 | 0.4 | — | 5 | 5 | 5 | 5 | 5 |
| | 0.2 | 1 | 5 | 5 | 5 | 4 | 5 |
| 54 | 0.4 | 1 | 5 | 5 | 5 | 5 | 5 |
| | 0.2 | 1 | 4 | 5 | 5 | 4 | 4 |
| 55 | 0.4 | — | 5 | 5 | 5 | 5 | 5 |
| | 0.2 | 1 | 5 | 5 | 5 | 4 | 5 |
| 56 | 0.4 | 1 | 5 | 5 | 5 | 5 | 5 |
| | 0.2 | 1 | 5 | 5 | 5 | 5 | 5 |
| 57 | 0.4 | 0 | 5 | 5 | 5 | 5 | 5 |
| | 0.2 | 0 | 5 | 5 | 5 | 4 | 4 |
| 58 | 0.4 | 1 | 5 | 5 | 5 | 5 | 5 |
| | 0.2 | 0 | 5 | 5 | 5 | 4 | 4 |
| 59 | 0.4 | 1 | 5 | 5 | 5 | 5 | 5 |
| | 0.2 | 0 | 5 | 5 | 5 | 5 | 5 |
| 60 | 0.4 | 0 | 5 | 5 | 5 | 5 | 5 |
| | 0.2 | 0 | 5 | 5 | 5 | 5 | 5 |
| 61 | 0.4 | 0 | 5 | 5 | 5 | 5 | 5 |
| | 0.2 | 0 | 5 | 5 | 5 | 5 | 5 |
| 62 | 0.4 | 1 | 5 | 5 | 5 | 5 | 5 |
| | 0.2 | 0 | 5 | 5 | 5 | 5 | 5 |
| 63 | 0.4 | 1 | 5 | 5 | 5 | 5 | 5 |
| | 0.2 | 0 | 5 | 5 | 5 | 5 | 5 |
| 64 | 0.4 | 1 | 5 | 5 | 5 | 5 | 5 |
| | 0.2 | 0 | 5 | 5 | 5 | 4 | 5 |
| 65 | 0.63 | 1 | 5 | 5 | 5 | 5 | 5 |
| | 0.16 | 0 | 4 | 5 | 5 | 5 | 5 |
| 66 | 0.4 | 1 | 5 | 5 | 5 | 5 | 5 |
| | 0.2 | 0 | 5 | 5 | 5 | 5 | 4 |
| 67 | 1.25 | — | 5 | 5 | 5 | 5 | 5 |
| | 0.32 | 1 | 5 | 5 | 5 | 5 | 4 |
| 68 | 0.4 | — | 5 | 5 | 5 | 5 | 5 |
| | 0.2 | 1 | 5 | 5 | 5 | 4 | 4 |
| 69 | 0.4 | 1 | 5 | 5 | 5 | 5 | 5 |
| | 0.2 | 1 | 5 | 5 | 5 | 5 | 4 |
| 70 | 1.25 | 1 | 5 | 5 | 5 | 5 | 5 |
| | 0.32 | 0 | 5 | 5 | 4 | 5 | 5 |
| 71 | 1.25 | 1 | 5 | 5 | 5 | 5 | 5 |
| | 0.32 | 1 | 5 | 5 | 5 | 5 | 5 |
| 72 | 0.4 | 1 | 5 | 5 | 5 | 5 | 5 |
| | 0.2 | 0 | 5 | 5 | 5 | 4 | 4 |
| 73 | 0.4 | 0 | 5 | 5 | 5 | 5 | 5 |
| | 0.2 | 0 | 4 | 5 | 5 | 4 | 4 |
| 74 | 0.4 | 1 | 5 | 5 | 5 | 5 | 5 |
| | 0.2 | 0 | 4 | 5 | 5 | 4 | 5 |
| 75 | 1.25 | 1 | 5 | 5 | 5 | 5 | 5 |
| | 0.32 | 0 | 5 | 5 | 5 | 5 | 5 |
| 76 | 1.25 | 1 | 5 | 5 | 5 | 5 | 5 |
| | 0.32 | 0 | 5 | 5 | 5 | 5 | 5 |
| 77 | 0.4 | 0 | 5 | 5 | 5 | 5 | 5 |
| | 0.2 | 0 | 5 | 5 | 5 | 4 | 5 |
| 78 | 0.4 | 2 | 5 | 5 | 5 | 5 | 5 |
| | 0.2 | 1 | 4 | 5 | 5 | 4 | 5 |
| 79 | 0.4 | 2 | 5 | 5 | 5 | 5 | 5 |
| | 0.2 | 1 | 5 | 5 | 5 | 4 | 4 |
| 80 | 0.4 | 2 | 5 | 5 | 5 | 5 | 5 |
| | 0.2 | 0 | 4 | 5 | 5 | 3 | 5 |
| 81 | 0.4 | 1 | 5 | 5 | 5 | 5 | 5 |
| | 0.2 | 1 | 5 | 5 | 5 | 4 | 5 |
| 82 | 0.4 | 1 | 5 | 5 | 5 | 5 | 5 |
| | 0.2 | 1 | 4 | 5 | 5 | 3 | 4 |
| 83 | 0.4 | 2 | 5 | 5 | 5 | 5 | 5 |
| | 0.2 | 0 | 4 | 5 | 5 | 4 | 4 |
| 84 | 0.4 | 1 | 5 | 5 | 5 | 5 | 5 |
| | 0.2 | 1 | 5 | 5 | 5 | 4 | 5 |
| 85 | 0.4 | 1 | 5 | 5 | 5 | 5 | 5 |
| | 0.2 | 1 | 4 | 5 | 5 | 4 | 5 |
| 86 | 0.4 | 2 | 5 | 5 | 5 | 5 | 5 |
| | 0.2 | 0 | 4 | 5 | 5 | 3 | 4 |
| 87 | 0.4 | 1 | 5 | 5 | 5 | 5 | 5 |
| | 0.2 | 1 | 4 | 5 | 5 | 4 | 5 |
| 88 | 0.4 | 2 | 5 | 5 | 5 | 5 | 5 |
| | 0.2 | 1 | 4 | 5 | 5 | 5 | 5 |
| 89 | 0.4 | 2 | 5 | 5 | 5 | 5 | 5 |
| | 0.2 | 1 | 5 | 5 | 5 | 4 | 4 |
| 90 | 0.4 | 2 | 5 | 5 | 5 | 5 | 5 |
| | 0.2 | 1 | 4 | 5 | 5 | 3 | 4 |
| 91 | 0.4 | 2 | 5 | 5 | 5 | 5 | 5 |
| | 0.2 | 1 | 5 | 5 | 5 | 4 | 5 |
| 92 | 0.8 | 2 | 5 | 5 | 5 | 5 | 5 |
| | 0.4 | 1 | 4 | 5 | 5 | 3 | 5 |
| 93 | 0.4 | 1 | 5 | 5 | 5 | 5 | 5 |
| | 0.2 | 0 | 5 | 5 | 5 | 4 | 5 |
| (a) | 0.4 | 3 | 4 | 5 | 4 | 3 | 2 |
| | 0.2 | 1 | 2 | 4 | 3 | 1 | 1 |
| (b) | 0.4 | 0 | 1 | 4 | 1 | 0 | 2 |
| (c) | 0.4 | 1 | 1 | 5 | 2 | 0 | 2 |
| (d) | 0.4 | 2 | 2 | 2 | 1 | 0 | 3 |
| (h) | 2.5 | 2 | 5 | 2 | 4 | 4 | 5 |
| | 0.63 | 0 | 3 | 0 | 1 | 1 | 5 |

Test Example 2

Wagner's pots (1/5000 are) are filled with field soil, and the seeds of tall morningglory, velvetleaf, redroot pigweed, soybean and corn are sowed therein and covered with soil to a depth of 1 cm. A designed amount of the test compound formulated into an emulsifiable concentrate and diluted with water is sprayed to the soil surface at a spray volume of 10 liters per are. The test plants are grown outdoors for 3 weeks, and herbicidal activity and phytotoxicity are examined. The results are shown in Table 3.

TABLE 3

| Compound No. | Dosage (weight of active ingredient, g/are) | Herbicidal activity | | | Phytotoxicity | |
|---|---|---|---|---|---|---|
| | | Tall morningglory | Velvetleaf | Redroot pigweed | Soybean | Corn |
| 1 | 20 | 5 | 5 | 5 | 0 | 0 |
| | 10 | 5 | 5 | 5 | 0 | 0 |
| 2 | 10 | 5 | 5 | 5 | 0 | 0 |
| | 5 | 5 | 5 | 5 | 0 | 0 |
| 13 | 10 | 5 | 5 | 5 | 0 | 0 |
| | 5 | 5 | 5 | 5 | 0 | 0 |
| 14 | 10 | 5 | 5 | 5 | 0 | 0 |
| | 5 | 5 | 5 | 5 | 0 | 0 |
| 15 | 10 | 5 | 5 | 5 | 0 | 0 |
| | 5 | 5 | 5 | 5 | 0 | 0 |
| 22 | 10 | 5 | 5 | 5 | 0 | 0 |
| | 5 | 5 | 5 | 5 | 0 | 0 |
| 24 | 10 | 5 | 5 | 5 | 0 | 0 |
| | 5 | 5 | 5 | 5 | 0 | 0 |
| 26 | 10 | 5 | 5 | 5 | 0 | 0 |
| | 5 | 5 | 5 | 5 | 0 | 0 |
| 29 | 10 | 5 | 5 | 5 | 0 | 0 |
| | 5 | 5 | 5 | 5 | 0 | 0 |
| 30 | 10 | 5 | 5 | 5 | 0 | 0 |
| | 5 | 5 | 5 | 5 | 0 | 0 |
| 31 | 10 | 5 | 5 | 5 | 0 | 0 |
| | 5 | 5 | 5 | 5 | 0 | 0 |
| 32 | 10 | 5 | 5 | 5 | 0 | 0 |
| | 5 | 5 | 5 | 5 | 0 | 0 |

TABLE 3-continued

| Compound No. | Dosage (weight of active ingredient, g/are) | Herbicidal activity Tall morning-glory | Velvet-leaf | Redroot pigweed | Phyto-toxicity Soybean | Corn |
|---|---|---|---|---|---|---|
| 34 | 10 | 5 | 5 | 5 | 0 | 0 |
|  | 5 | 5 | 5 | 5 | 0 | 0 |
| 35 | 10 | 5 | 5 | 5 | 0 | 0 |
|  | 5 | 5 | 5 | 5 | 0 | 0 |
| 44 | 20 | 5 | 5 | 5 | 0 | 0 |
|  | 10 | 5 | 5 | 5 | 0 | 0 |
| 45 | 20 | 5 | 5 | 5 | 0 | 0 |
|  | 10 | 5 | 5 | 5 | 0 | 0 |
| 47 | 10 | 5 | 5 | 5 | 0 | 0 |
|  | 5 | 5 | 5 | 5 | 0 | 0 |
| 48 | 20 | 5 | 5 | 5 | 0 | 0 |
|  | 10 | 5 | 5 | 5 | 0 | 0 |
| 49 | 10 | 5 | 5 | 5 | 0 | 0 |
|  | 5 | 5 | 5 | 5 | 0 | 0 |
| 51 | 10 | 5 | 5 | 5 | 0 | 0 |
|  | 5 | 5 | 5 | 5 | 0 | 0 |
| 52 | 10 | 5 | 5 | 5 | 0 | 0 |
|  | 5 | 5 | 5 | 5 | 0 | 0 |
| 57 | 10 | 5 | 5 | 5 | 0 | 0 |
|  | 5 | 5 | 5 | 5 | 0 | 0 |
| 63 | 10 | 5 | 5 | 5 | 0 | 0 |
|  | 5 | 5 | 5 | 5 | 0 | 0 |
| 64 | 10 | 5 | 5 | 5 | 0 | 0 |
|  | 5 | 5 | 5 | 5 | 0 | 0 |

Test Example 3

Plastic pots (diameter, 10 cm; height, 10 cm) are filled with upland field soil, and the seeds of soybean, cotton, tall morningglory and velvetleaf are sowed therein and covered with soil. A designed amount of the test compound formulated into an emulsifiable concentrate and diluted with water is sprayed to the soil at a spray volume of 10 liters per are and then the soil is well mixed to a depth of 4 cm. The test plants are further grown for 20 days in a greenhouse, and herbicidal activity and phytotoxicity are examined. The results are shown in Table 4.

TABLE 4

| Compound No. | Dosage (weight of active ingredient, g/are) | Herbicidal activity Tall morning-glory | Velvet-leaf | Phyto-toxicity Soybean | Cotton |
|---|---|---|---|---|---|
| 67 | 20 | 5 | 5 | 0 | 2 |
|  | 5 | 5 | 5 | 0 | 0 |
| 68 | 20 | 5 | 5 | 0 | 1 |
|  | 5 | 4 | 5 | 0 | 0 |
| 69 | 20 | 5 | 5 | 0 | 2 |
|  | 5 | 5 | 5 | 0 | 0 |
| 70 | 20 | 5 | 5 | 0 | 0 |
| 71 | 20 | 5 | 5 | 0 | 2 |
|  | 5 | 5 | 5 | 0 | 1 |
| 72 | 20 | 5 | 5 | 0 | 0 |
| 73 | 20 | 5 | 5 | 0 | 0 |
| 74 | 20 | 5 | 5 | 0 | 0 |
| 75 | 20 | 5 | 5 | 0 | 2 |
|  | 5 | 5 | 5 | 0 | 0 |
| 76 | 20 | 5 | 5 | 0 | 0 |
| 77 | 20 | 5 | 5 | 0 | 0 |
| 78 | 20 | 5 | 5 | 0 | 1 |
| 89 | 20 | 5 | 5 | 0 | 2 |
| 91 | 20 | 5 | 5 | 0 | 1 |
| 92 | 20 | 5 | 5 | 0 | 0 |
| 93 | 20 | 5 | 5 | 0 | 1 |
|  | 5 | 5 | 5 | 0 | 0 |

Test Example 4

Plastic pots (diameter, 8 cm; height, 12 cm) filled with paddy field soil, and the seeds of barnyardgrass and broad-leaved weeds (e.g. false pimpernel, toothcup, waterwort) are sowed therein to a depth of 1 to 2 cm. The pots are placed under a flooded condition, and the tubers of arrowhead and the rice seedlings of the 2-leaf stage are transplanted therein at a depth of 1 to 2 cm and grown for 6 days in a greenhouse. A designed amount of the test compound formulated into an emulsifiable concentrate and diluted with water was perfused into the pots at a perfusion volume of 5 ml per pot. The test plants are further grown for 20 days in the greenhouse, and phytotoxicity and herbicidal activity are examined. The results are shown in Table 5.

TABLE 5

| Compound No. | Dosage (weight of active ingredient, g/are) | Herbicidal activity Barnyard-glass | Broad-leaved weed | Arrow-head | Phyto-toxicity Rice plant |
|---|---|---|---|---|---|
| 26 | 5 | 4 | 5 | 4 | 1 |
| 44 | 5 | 3 | 5 | 5 | 1 |
| 48 | 5 | 3 | 5 | 4 | 1 |
| 51 | 5 | 4 | 5 | 5 | 1 |
| 67 | 10 | 5 | 5 | 4 | 1 |
| 68 | 10 | 4 | 5 | 5 | 0 |
| 71 | 10 | 5 | 5 | 5 | 1 |
| 75 | 10 | 5 | 5 | 5 | 1 |
| 89 | 10 | 4 | 5 | 5 | 0 |
| 91 | 10 | 5 | 5 | 5 | 1 |
| 93 | 10 | 4 | 5 | 4 | 0 |

Test Example 5

The seeds of soybean, cocklebur, tall morningglory, velvetleaf, jimson weed, redroot pigweed, sunflower, common ragweed and common lambsquarters are sowed in the field as previously laid up in ridges, each ridge being plotted in 3 m². When soybean, cocklebur and other plants are grown at the 1-2 compound leaf stage, 6-leaf stage and 4-9 leaf stage, respectively, a designed amount of the test compound formulated into an emulsifiable concentrate and diluted with water (including a spreading agent) is sprayed to the foliage of the test plants by means of a small hand sprayer at a spray volume of 5 liters per are with three replications. Thirty days thereafter, herbicidal activity and phytotoxicity are examined. The results are shown in Table 6.

TABLE 6

| Compound No. | Dosage (weight of active ingredient, g/are) | Phyto-toxicity Soybean | Herbicidal activity Cocklebur | Tall morningglory | Velvet-leaf | Jimson weed | Redroot pigweed | Sun-flower | Common ragweed | Common lambsquarters |
|---|---|---|---|---|---|---|---|---|---|---|
| 1 | 1 | 1 | 5 | 5 | 5 | 5 | 5 | 5 | 5 | 5 |
|  | 0.5 | 1 | 4 | 5 | 5 | 5 | 5 | 5 | 5 | 5 |

TABLE 6-continued

| Compound No. | Dosage (weight of active ingredient, g/are) | Phyto- toxicity Soybean | Herbicidal activity | | | | | | | |
|---|---|---|---|---|---|---|---|---|---|---|
| | | | Cocklebur | Tall morningglory | Velvet- leaf | Jimson weed | Redroot pigweed | Sun- flower | Common ragweed | Common lambsquarters |
| 8 | 1 | 1 | 5 | 5 | 5 | 5 | 5 | 5 | 5 | 5 |
| | 0.5 | 0 | 5 | 5 | 5 | 5 | 5 | 5 | 5 | 5 |
| 13 | 1 | 1 | 5 | 5 | 5 | 5 | 5 | 5 | 5 | 5 |
| | 0.5 | 0 | 5 | 5 | 5 | 5 | 5 | 5 | 5 | 4 |
| 30 | 1 | 1 | 5 | 5 | 5 | 5 | 5 | 5 | 5 | 5 |
| | 0.5 | 0 | 4 | 5 | 5 | 5 | 5 | 4 | 5 | 5 |
| (e) | 10 | 1 | 5 | 3 | 5 | 5 | 2 | 5 | 5 | 5 |
| | 5 | 0 | 5 | 1 | 5 | 5 | 0 | 5 | 5 | 3 |

Test Example 6

The seeds of corn, cocklebur, tall morningglory, velvetleaf, jimson weed and redroot pigwood are sowed in the field as previously laid up in ridges, each ridge being plotted in 3 m². When corn, cocklebur and other plants are grown at the 6-7 leaf stage, 4-leaf stage and 3-6 leaf stage, respectively, a designed amount of the test compound formulated into an emulsifiable concentrate and diluted with water (including a spreading agent) is sprayed to the foliage of the test plants by means of a small hand sprayer at a spray volume of 5 liters per are with three replications. Thirty days thereafter, herbicidal activity and phytotoxicity are examined. The results are shown in Table 7.

TABLE 7

| Compound No. | Dosage (weight of active ingredient, g/are) | Phyto- toxicity Corn | Herbicidal activity | | | | |
|---|---|---|---|---|---|---|---|
| | | | Cocklebur | Tall morningglory | Velvet- leaf | Jimson weed | Redroot pigweed |
| 1 | 1 | 1 | 5 | 5 | 5 | 5 | 5 |
| | 0.5 | 0 | 5 | 5 | 5 | 5 | 5 |
| 8 | 1 | 1 | 5 | 5 | 5 | 5 | 5 |
| | 0.5 | 1 | 4 | 5 | 5 | 5 | 5 |
| (f) | 10 | 1 | 5 | 5 | 5 | 5 | 5 |
| | 5 | 0 | 5 | 4 | 4 | 5 | 4 |

Test Example 7

Seeds of soybean, tall morningglory, velvetleaf, common lambsquarters, redroot pigweed, black nightshade, common ragweed and common purslane are sowed in the field as previously laid up in ridges, each ridge being plotted in 3 m². A designed amount of the test compound formulated into an emulsifiable concentrate and diluted with water (including a spreading agent) is sprayed to the soil surface by means of a small hand sprayer at a spray volume of 5 liters per are with three replications. Thirty days thereafter, herbicidal activity and phytotoxicity are examined. The results are shown in Table 8.

TABLE 8

| Compound No. | Dosage (weight of active ingredient, g/are) | Phyto- toxicity Soybean | Herbicidal activity | | | | | | |
|---|---|---|---|---|---|---|---|---|---|
| | | | Tall morningglory | Velvet- leaf | Common lambsquarters | Redroot pigweed | Black nightshade | Common ragweed | Common purslane |
| 13 | 16 | 0 | 5 | 5 | 5 | 5 | 5 | 5 | 5 |
| | 8 | 0 | 4 | 5 | 5 | 5 | 5 | 4 | 5 |
| (g) | 8 | 1 | 3 | 5 | 5 | 5 | 3 | 5 | 5 |
| | 4 | 0 | 1 | 4 | 4 | 5 | 1 | 4 | 5 |

What is claimed is:

1. A compound of the formula:

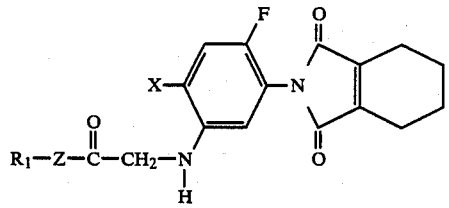

wherein $R_1$ is hydrogen, alkyl, lower cycloalkyl, lower alkyl(lower)cycloalkyl, lower cycloalkyl(lower)alkyl, lower alkoxy(lower)alkyl, lower alkenyl, lower cycloalkenyl, lower cycloalkenyl(lower)alkyl, phenyl, cyano(lower)alkyl, lower alkynyl, lower alkylideneamino, lower alkylthio(lower)alkyl, benzyl, halo(lower)alkyl or lower cycloalkylideneamino, X is chlorine or bromine and Z is oxygen or sulfur.

2. The compound according to claim 1, wherein Z is oxygen.

3. The compound according to claim 1, which is [2-(4-chloro-2-fluoro-5-cyclopentyloxycarbonylmethyliminophenyl)-4,5,6,7-tetrahydro-2H-isoindole-1,3-dione] 2-(4-chloro-2-fluoro-5-cyclopentyloxycarbonylmethylaminophenyl)-4,5,6,7-tetrahydro-2H-isoindole-1,3-dione.

4. A herbicidal composition which comprises a herbicidally effective amount of a compound of the formula:

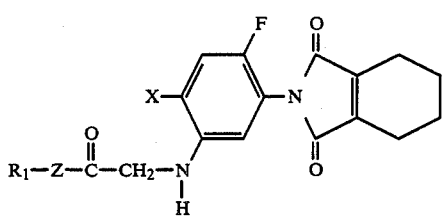

wherein $R_1$ is hydrogen, alkyl, lower cycloalkyl, lower alkyl(lower)cycloalkyl, lower cycloalkyl(lower)alkyl, lower alkoxy(lower)alkyl, lower alkenyl, lower cycloalkenyl, lower cycloalkenyl(lower)alkyl, phenyl, cyano(lower)alkyl, lower alkynyl, lower alkylideneamino, lower alkylthio(lower)alkyl, benzyl, halo(lower)alkyl or lower cycloalkylideneamino, X is chlorine or bromine and Z is oxygen or sulfur as an active ingredient and an inert carrier.

5. The composition according to claim 4, wherein Z is oxygen.

6. The composition according to claim 4, wherein the compound is [2-(4-chloro-2-fluoro-5-cyclopentyloxycarbonyl-aminophenyl)-4,5,6,7-tetrahydro-2H-isoindole-1,3-dione] 2-(4-chloro-2-fluoro-5-cyclopentyloxycarbonylmethylaminophenyl)-4,5,6,7-tetrahydro-2H-isoindole-1,3-dione.

7. The composition according to claim 4, wherein the compound is [2-(4-chloro-2-fluoro-5-ethoxycarbonylmethyliminophenyl)-4,5,6,7-tetrahydro-2H-isoindole-1,3-dione] 2-(4-chloro-2-fluoro-5-ethoxy-carbonylmethylaminophenyl)-4,5,6,7-tetrahydro-2H-isoindole-1,3-dione.

8. A method for controlling or exterminating weeds in a field which comprises applying, to an area where weeds grow or will grow, a herbicidally effective amount of a compound of the formula:

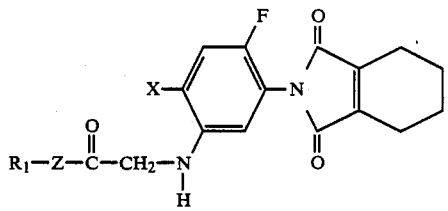

wherein $R_1$ is hydrogen, alkyl, lower cycloalkyl, lower alkyl(lower)cycloalkyl, lower cycloalkyl(lower)alkyl, lower alkoxy(lower)alkyl, lower alkenyl, lower cycloalkenyl, lower cycloalkenyl(lower)alkyl, phenyl, cyano(lower)alkyl, lower alkynyl, lower alkylideneamino, lower alkylthio(lower)alkyl, benzyl, halo(lower)alkyl or lower cycloalkylideneamino, X is chlorine or bromine and Z is oxygen or sulfur.

9. The method according to claim 8, wherein Z is oxygen.

10. The method according to claim 8, wherein the compound is [2-(4-chloro-2-fluoro-5-cyclopentyloxycarbonylmethoxyphenyl)-4,5,6,7-tetrahydro-2H-isoindole-1,3-dione] 2-(4-chloro-2-fluoro-5-cyclopentyloxycarbonylmethylaminophenyl)-4,5,6,7-tetrahydro-2H-isoindole-1,3-dione.

11. The method according to claim 8, wherein the compound is [2-(4-chloro-2-fluoro-5-ethoxycarbonylmethyliminophenyl)-4,5,6,7-tetrahydro-2H-isoindole-1,3dione] 2-(4-chloro-2-fluoro-5-ethoxycarbonylmethylaminophenyl)-4,5,6,7-tetrahydro-2H-isoindole-1,3-dione.

12. The method according to claim 8, wherein the field is a corn or a soybean field.

13. The method according to claim 8, wherein the field is a soybean field.

14. The method according to claim 8, wherein said compound is applied by post-emergence treatment.

15. The method according to claim 14, wherein said dosage is from 0.1 to 1.25 grams per are.

16. The method according to claim 14, wherein said dosage is from 0.1 to 0.8 grams per are.

17. The method according to claim 14, wherein said doage is from 0.2 to 0.4 grams per are.

18. The method according to claim 14, wherein the field is a soybean field.

19. The method according to claim 15, wherein the field is a soybean field.

20. The method according to claim 16, wherein the field is a soybean field.

21. The method according to claim 17, wherein the field is a soybean field.

* * * * *